(12) United States Patent
Cassidy

(10) Patent No.: US 8,378,832 B2
(45) Date of Patent: Feb. 19, 2013

(54) BREATHING DISORDER TREATMENT SYSTEM AND METHOD

(76) Inventor: Harry J. Cassidy, Menlo Park, CA (US)

(*) Notice: Subject to any disclaimer, the term of this patent is extended or adjusted under 35 U.S.C. 154(b) by 499 days.

(21) Appl. No.: 12/659,483

(22) Filed: Mar. 10, 2010

(65) Prior Publication Data

US 2011/0006901 A1    Jan. 13, 2011

Related U.S. Application Data

(60) Provisional application No. 61/213,740, filed on Jul. 9, 2009.

(51) Int. Cl.
*G08G 23/00* (2006.01)
(52) U.S. Cl. .................................... 340/573.1
(58) Field of Classification Search .......... 340/573.1, 340/575, 620, 309.16, 384.1; 128/200.24; 600/484, 529
See application file for complete search history.

(56) References Cited

U.S. PATENT DOCUMENTS

| | | | |
|---|---|---|---|
| 5,365,922 A * | 11/1994 | Raemer | 128/204.23 |
| 5,769,084 A * | 6/1998 | Katz et al. | 600/513 |
| 5,978,691 A | 11/1999 | Mills | |
| 6,681,454 B2 * | 1/2004 | Modgil et al. | 24/306 |
| 7,169,110 B2 * | 1/2007 | Lee et al. | 600/484 |
| 7,222,624 B2 | 5/2007 | Rashad et al. | |
| 7,297,119 B2 * | 11/2007 | Westbrook et al. | 600/529 |
| 7,470,234 B1 | 12/2008 | Elhag et al. | |
| 7,499,740 B2 | 3/2009 | Nordstrom et al. | |
| 7,803,119 B2 * | 9/2010 | Reisfeld | 600/483 |
| 8,255,056 B2 * | 8/2012 | Tehrani | 607/42 |
| 2004/0116784 A1 * | 6/2004 | Gavish | 600/300 |
| 2006/0011199 A1 | 1/2006 | Rashad et al. | |
| 2006/0229511 A1 | 10/2006 | Fein et al. | |
| 2008/0078384 A1 | 4/2008 | Messenger et al. | |
| 2008/0178882 A1 | 7/2008 | Christopher et al. | |
| 2008/0183057 A1 | 7/2008 | Taube | |
| 2008/0295839 A1 | 12/2008 | Habashi | |

FOREIGN PATENT DOCUMENTS

| | | |
|---|---|---|
| CN | 1559342 A | 1/2005 |
| JP | 2005-245825 A | 9/2005 |
| WO | WO 2008/058328 A1 | 5/2008 |

* cited by examiner

*Primary Examiner* — Phung Nguyen
(74) *Attorney, Agent, or Firm* — Richard C. Litman

(57) ABSTRACT

The breathing disorder treatment system is a continuous monitoring and an actuated stimulation system for the treatment of breathing disorders, such as sleep apnea. The system includes computer readable memory in communication with a processor, and a threshold blood oxygen saturation (BOS) level is recorded therein. A BOS sensor is provided for continually measuring the blood oxygen saturation level in the patient. The BOS sensor is in communication with the processor, such that the measured BOS level is continually compared with the threshold BOS level. A timer is in communication with the processor, so that if a series of measured BOS levels are less than or equal to the threshold BOS level, a time of apnea or low BOS occurrence is recorded in the memory, and an alarm is actuated according to a calculated moving average period based upon the times of occurrence.

12 Claims, 3 Drawing Sheets

BREATHING DISORDER TREATMENT SYSTEM AND METHOD

CROSS-REFERENCE TO RELATED APPLICATION

This application claims the benefit of U.S. Provisional Patent Application Ser. No. 61/213,740, filed Jul. 9, 2009.

BACKGROUND OF THE INVENTION

1. Field of the Invention

The present invention relates to sleep monitoring systems, and particularly to a breathing disorder treatment system and method that provides a continuous monitoring and an actuated stimulation system for the treatment of sleep disorders, such as sleep apnea, and other medical disorders and conditions that adversely affect a patient's breathing.

2. Description of the Related Art

Sleep apnea is a sleep disorder characterized by pauses in breathing during sleep. Each episode, referred to as an "apnea", lasts long enough so that one or more breaths are missed, and such episodes occur repeatedly throughout sleep. The standard definition of any apnea event includes a minimum ten second interval between breaths, with either a neurological arousal, a blood oxygen desaturation of 3 to 4% or greater, or both arousal and desaturation. Sleep apnea is typically diagnosed by an overnight sleep test called a polysomnogram. Sleep apnea not only affects the sufferer, but due to snoring and other noises associated with apnea, others in the vicinity of the sleeper may be adversely affected due to the disturbed sleep.

Clinically significant levels of sleep apnea are defined as five or more episodes per hour of any type of apnea (determined by the polysomnogram). There are three distinct forms of sleep apnea, including central, obstructive, and complex (i.e., a combination of central and obstructive), constituting 0.4%, 84% and 15% of cases, respectively. Breathing is interrupted by the lack of respiratory effort in central sleep apnea. In obstructive sleep apnea, breathing is interrupted by a physical block to airflow despite respiratory effort. In complex (or "mixed") sleep apnea, there is a transition from central to obstructive features during the events themselves.

The most common treatment for obstructive sleep apnea is the use of a continuous positive airway pressure (CPAP) device, which "splints" the patient's airway open during sleep via a flow of pressurized air into the throat. Such systems, however, are rather bulky and uncomfortable for the user. Until the user becomes accustomed to the CPAP device, he or she may be kept awake by the machine that is designed to aid him or her in sleeping properly.

In addition to CPAP, a dentist specializing in sleep disorders may prescribe Oral Appliance Therapy (OAT). The oral appliance is a custom-made mouthpiece that shifts the lower jaw forward, which opens up the airway. OAT is usually successful in patients with mild to moderate obstructive sleep apnea, but can cause tempomendibular joint disfunction, loosening or breakage of teeth, veneers, crowns, caps, and implants. As with CPAP, the OAT may prevent the user from gaining a good night's sleep until he or she becomes accustomed to the awkwardness of the device. It should be noted that CPAP and OAT are effective only for obstructive sleep apnea, not for central or mixed cases.

For patients who do not tolerate or who fail non-surgical measures, surgical treatment to anatomically alter the airway is available. Several levels of obstruction may be addressed, including the nasal passage, throat (pharynx), base of tongue, and facial skeleton. Surgical treatment for obstructive sleep apnea needs to be individualized in order to address all anatomical areas of obstruction. Often, correction of the nasal passages needs to be performed, in addition to correction of the oropharynx passage.

Septoplasty and turbinate surgery may improve the nasal airway. Tonsillectomy and uvulopalatopharyngoplasty (UPPP or UP3) is available to address pharyngeal obstruction. Base of tongue advancement by means of advancing the genial tubercle of the mandible may help with the lower pharynx. A myriad of other techniques are available, including hyoid bone myotomy and suspension and various radiofrequency technologies. For patients who fail these operations, the facial skeletal may be advanced by means of a technique called maxillo-mandibular advancement, or two-jaw surgery (upper and lower jaws). The surgery involves a Lefort type one osteotomy and bilateral sagittal split mandibular osteotomies. Such severe treatments, however, come with the typical risks and discomforts of major surgery.

It should be noted that sleep apnea is not simply an inconvenience for the sufferer. Many drugs and agents used during surgery to relieve pain and to depress consciousness remain in the body at low amounts for hours or even days afterwards. In an individual with either central, obstructive or mixed sleep apnea, these low doses may be enough to cause life-threatening irregularities in breathing.

Use of analgesics and sedatives in these patients postoperatively should therefore be minimized or avoided. Surgery on the mouth and throat, as well as dental surgery and procedures, can result in postoperative swelling of the lining of the mouth and other areas that affect the airway. Even when the surgical procedure is designed to improve the airway, such as tonsillectomy and adenoidectomy or tongue reduction, swelling may negate some of the effects in the immediate postoperative period. Once the swelling resolves and the palate becomes tightened by postoperative scarring however, the full benefit of the surgery may be noticed. Individuals with sleep apnea generally require more intensive monitoring after surgery for these reasons.

For the complex variety of other respiratory ailments, each is specifically treated as needed with antibiotics, supplemental oxygen, aerobic exercise, corticosteroids, short-term use of ventilators or a host of other treatment options. Benefits from these treatments must be monitored for their effectiveness. A common symptom for respiratory distress is lower than required blood oxygen. Thus, a blood oxygen saturation (BOS) monitoring and treatment system would be beneficial for providing an early warning when measured BOS equals or is below a set value. Thus, a breathing disorder treatment system and method solving the aforementioned problems is desired.

SUMMARY OF THE INVENTION

The breathing disorder treatment system is a continuous monitoring and an actuated stimulation system for the treatment of sleep disorders, such as sleep apnea and other medical disorders and conditions that interfere with or interrupt a patient's breathing. Input to the system may include patient information, an established threshold BOS, and a pre-selected period of time for temporary deactivation of the alarm system. Output from the system may include a signal to actuate an alarm, along with data recorded in the system's memory. The system includes a processor, which may be associated with a computer located near the patient, or which may be incorporated into a separate device, such as a programmable logic controller or the like, or may be integrated with the monitoring and/or stimulus system. Computer readable memory, which may be any suitable type of computer readable memory or media, is in communication with the processor, and a threshold blood oxygen saturation level is recorded in the computer readable memory. The threshold blood oxygen saturation level is a predetermined blood oxygen saturation percentage, representing an acceptable healthy level for the particular patient during a specific phase of treatment.

A blood oxygen saturation sensor is provided for continually measuring the blood oxygen saturation level in the patient. The blood oxygen saturation sensor may be an oximeter or any other suitable device for measuring the blood oxygen saturation of the patient. The blood oxygen saturation sensor is in communication with the processor, so that the measured blood oxygen saturation level is continually compared with the threshold blood oxygen saturation level.

A timer or clock is in communication with the processor. If the measured blood oxygen saturation level is less than or equal to the threshold blood oxygen saturation level, an apnea occurrence (or a low BOS occurrence, for non-apnea related disorders) and the time it happened is recorded in the computer readable memory. Additionally, all BOS and time values may be recorded along with the threshold value. This history may then be downloaded to portable devices or other conventional memory systems using any conventional interface, such as a universal serial bus (USB) interface, a wireless interface or the like. The historical record may be used in the accurate diagnosis of a particular medical condition, particularly when used in conjunction with other medical tests.

The processor calculates a time period between sequential times of apnea or low BOS occurrence. The system includes a stimulation alarm in communication with the processor. The alarm may be electrical or vibratory, including auditory and pulsed alarms, or may be an implantable, electrical stimulation device or the like, with the stimulation raising the patient's level of consciousness. The processor generates an alarm signal that actuates the alarm, which may be at regular intervals based upon the calculated time period between low blood oxygen saturation occurrences to raise the patient's level of consciousness. Alternatively, the alarm signal may be generated directly from the measured BOS being equal or below the threshold BOS. The present system alerts the patient when low BOS is detected.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
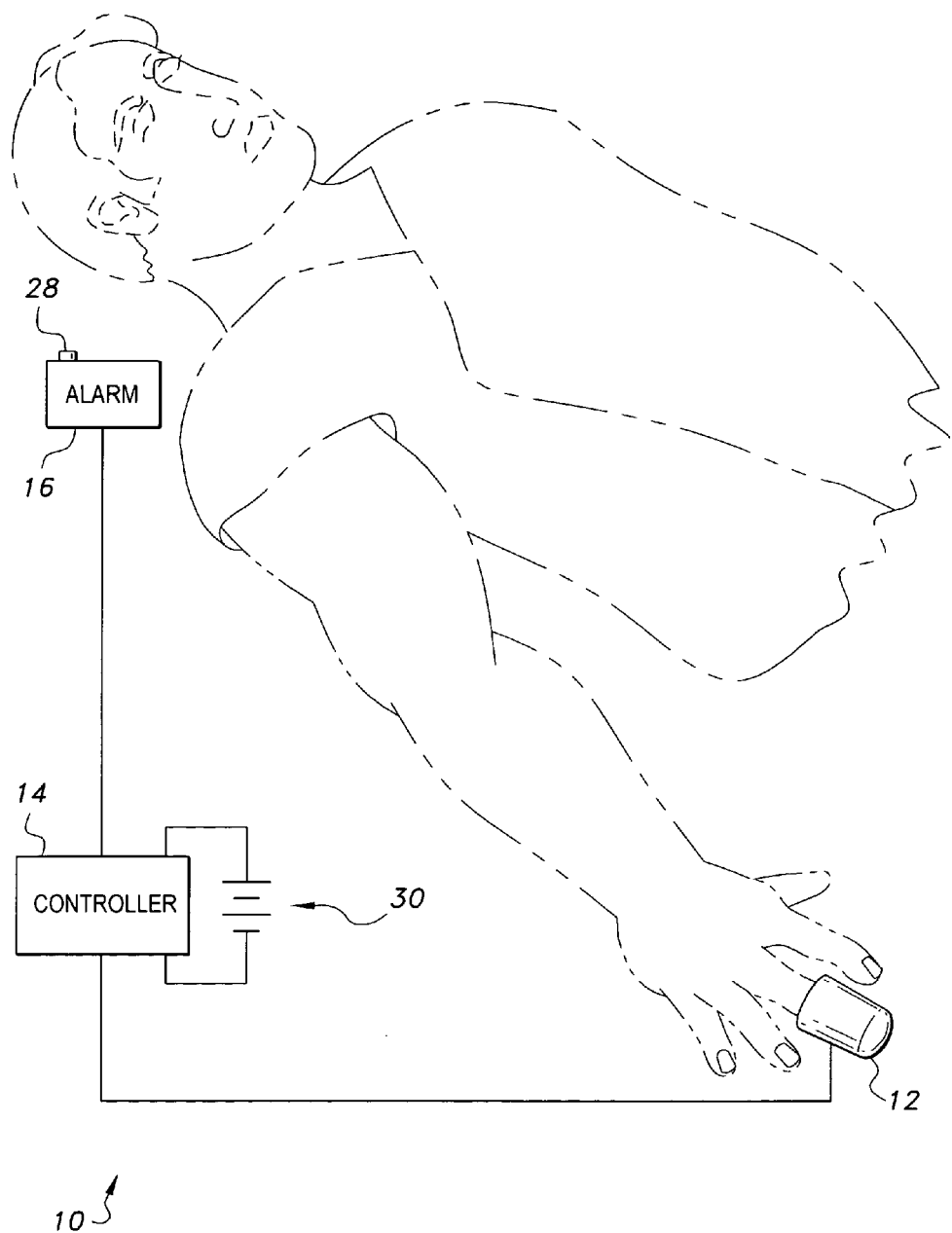
FIG. 1 is a diagrammatic overview of a breathing disorder treatment system according to the present invention.
Figure 2:
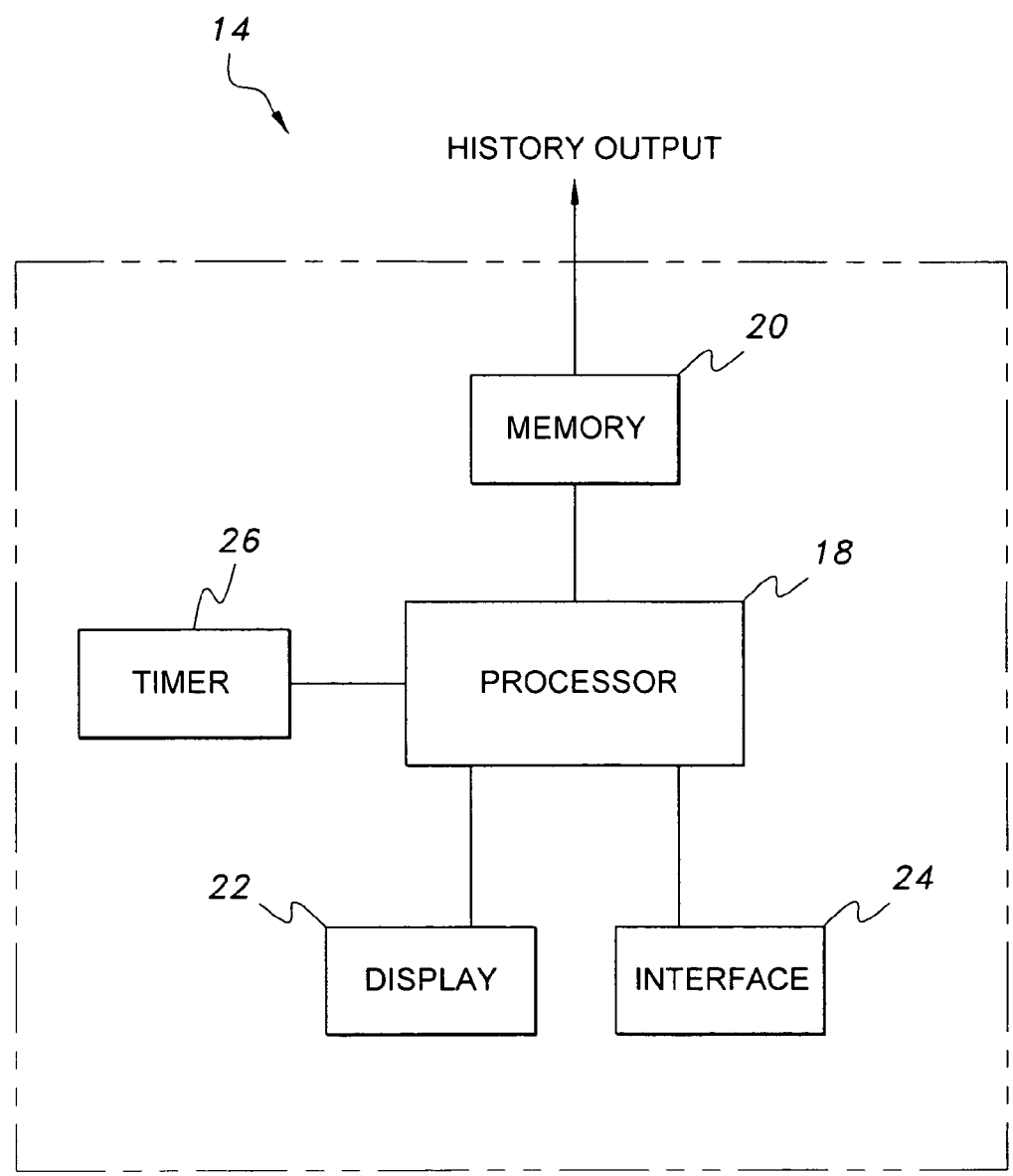
FIG. 2 is a block diagram illustrating a controller in a breathing disorder treatment system according to the present invention.
Figure 3:
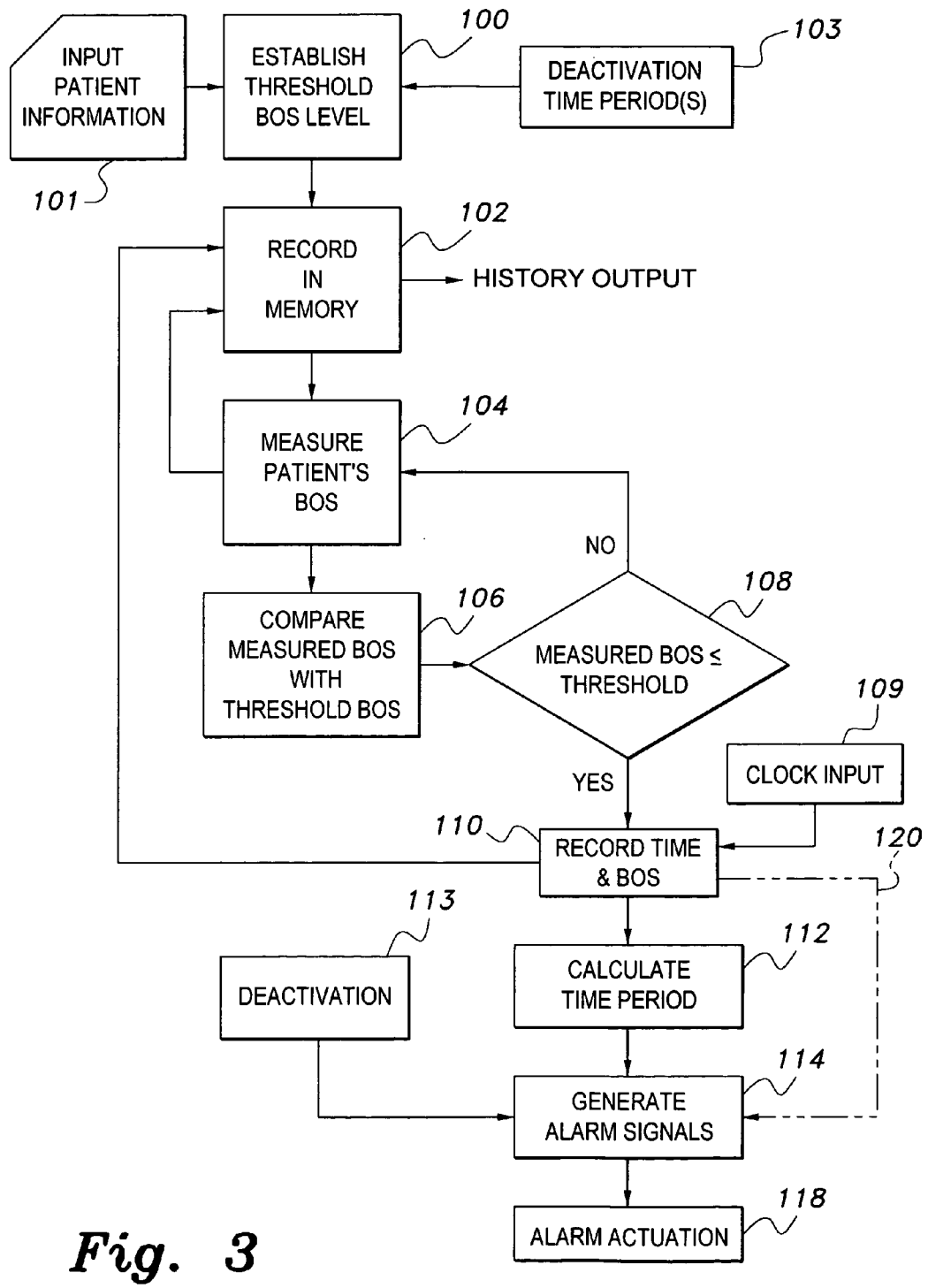
FIG. 3 is a flowchart illustrating the steps of the breathing disorder treatment method.

Referring to FIGS. 1 and 2, the breathing disorder treatment system 10 is a continuous monitoring and an actuated stimulation system for the treatment of breathing disorders, such as sleep apnea and other medical disorders and conditions that disrupt or interrupt a patient's breathing, or for any other condition resulting in a patient's low BOS levels. As shown in FIG. 1, the system 10 includes a controller 14, which is mounted by the patient's bedside. It should be understood that the bedside mounting of controller 14 is shown for exemplary purposes only, and that controller 14, as will be described below, may have a wide variety of configurations, and may be mounted on the user or have any other suitable configuration and mounting. As shown in FIG. 2, the controller 14 includes a processor 18, which may be the central processing unit of a control computer, or may be incorporated into a separate device, such as a programmable logic controller or the like. Computer readable memory 20, which may be any suitable type of computer readable memory or media, is in communication with the processor 18, and a threshold blood oxygen saturation (BOS) level is recorded in the computer readable memory 20 (establishment of the BOS is shown as step 100 in FIG. 3, and the recordation thereof in memory 20 is shown as step 102). Additionally, at step 101, the patient may input additional information, such as preferred language, body weight, medical history and other patient-specific data, to be recorded in memory 20. Further, the patient may also input a pre-selected period of time for the temporary deactivation of the alarm system (step 103). For example, as previously described with relation to sleep apnea, sleep apnea may be at least partially defined as a condition that includes a minimum of at least ten seconds between breaths. Thus, the interval of time allowed at step 103 may be between zero and ten seconds (in this example), and the period of time selected as input may be eight seconds. Time intervals allowed, and the input time period selected, may vary based upon the specific breathing disorder under consideration.

The threshold blood oxygen saturation level is a predetermined blood oxygen saturation percentage, representing an acceptable, healthy level for the particular patient. A computer display 22 and user interface 24 may also be provided, with both being in communication with processor 18. It should be understood that any suitable type of processor, memory, display and interface may be utilized. Similarly, any suitable type of power source 30 (and any suitable type of on-off means) may be utilized, dependent upon the nature of the controller 14. Additionally, any suitable type of connection between controller 14, alarm 16 and sensor 12 (to be described in detail below) may be used, such as wired connections, wireless connections or networked connections, or, alternatively, the individual components may be integrated into one or more units, which may be either worn by the user, or positioned near the user. While primarily considered for sleep apnea, the present invention relates to blood oxygen monitoring systems, and particularly to a system and method that provides a continuous monitoring and an actuated stimulation system for the treatment of any respiratory disorder, such as sleep apnea, age-related lung capacity reduction, asthma, emphysema, partial lung removal, and other medical disorders and conditions that may lower blood oxygen saturation (BOS). This includes post-surgery recovery, and the recovery period for acute bronchitis, pleurisy, tuberculosis, lung abscess, and other respiratory distresses.

A blood oxygen saturation sensor 12 is provided for continually measuring the blood oxygen saturation level in the patient. The blood oxygen saturation sensor 12 may be an oximeter, such as a pulse oximeter, or any other suitable device for measuring the blood oxygen saturation of the patient. Oximetry is a non-invasive method for monitoring oxygenation of a patient's hemoglobin. Typically, a sensor is placed on a thin part of the patient's anatomy, such as a fingertip (as illustrated in FIG. 1) or an earlobe, finger, toe or the like, and a light containing both red and infrared wavelengths is passed from one side to the other. Changing absorbance of each of the two wavelengths is measured, allowing determination of the absorbances due to the pulsing arterial blood alone, excluding venous blood, skin, bone, muscle, fat, and (in most cases) fingernail polish. Based upon the ratio of changing absorbance of the red and infrared light caused by the difference in color between oxygen-bound hemoglobin (bright red) and oxygen unbound (dark red or blue, in severe cases) blood hemoglobin, a measure of oxygenation (the percent of hemoglobin molecules bound with oxygen molecules) can be made.

At low partial pressures of oxygen, most hemoglobin is deoxygenated. At around 90% (the value varies according to the clinical context), oxygen saturation increases according to an oxygen-hemoglobin dissociation curve and approaches 100% at partial oxygen pressures of greater than 10 kPa. An oximeter relies on the light absorption characteristics of saturated hemoglobin to give an indication of oxygen saturation, as described above. An $S_aO_2$ (arterial oxygen saturation) value below 90% causes hypoxemia (which can also be caused by anemia). Hypoxemia due to low $S_aO_2$ is indicated by cyanosis.

The $S_vO_2$ (venous oxygen saturation) is typically measured to see how much oxygen the body consumes. Under clinical treatment, an $S_vO_2$ below 60% indicates that the body is in lack of oxygen, and ischemic diseases occur. This measurement is often used under treatment with a heart-lung machine (Extra Corporal Circulation), and can give the perfusionist an idea of how much flow the patient needs to stay healthy.

Saturation of Peripheral Oxygen ($S_pO_2$) is an estimation of the oxygen saturation level usually measured with an oximeter device. It should be understood that the blood oxygen saturation sensor 12 may be any suitable type of sensor for measuring the BOS of the patient. The blood oxygen saturation sensor 12 is in communication with the processor 18, so that the measured blood oxygen saturation level is continually compared with the threshold blood oxygen saturation level (steps 106, 108 in FIG. 3). Sensor 12 is shown for exemplary purposes only in FIG. 1, and may be any suitable type of BOS sensor fixed to any desired portion of the patient's body. Additionally, sensor 12 may be integrated into a holder or a modified item of clothing, such as a glove, hat, stocking, sleeve or mitten, or may be attached by the use of any suitable type of adhesives or any other suitable types of attachment.

As shown in FIG. 2, a timer 26, clock circuit (with a suitable power source), or timing circuit is in communication with the processor 18. If the measured blood oxygen saturation level (measured at step 104 in FIG. 3) is less than or equal to the threshold blood oxygen saturation level (steps 106 and 108), an apnea occurrence (or low-BOS occurrence, for non-apnea related conditions causing a low BOS in the patient) and the time of the occurrence is recorded in the computer readable memory 20 (step 110). As noted above, the system may also include a deactivation timer, and this timer has a conventional clock circuit associated therewith. Such a clock circuit, which is part of timer 26, provides time input at step 109 such that the incidents may recorded by time. Additionally, at step 110, all values of BOS and time may be recorded. The history of these occurrences may be downloaded to a portable device or other form of computer readable memory, as noted above. The processor 18 may also calculate a time period between sequential times of low-BOS occurrence (step 112) by taking a difference between sequential recordations made at step 110.

The system 10 includes an alarm 16 in communication with the processor 18 of controller 14. The alarm 16 may be an applied electrical stimulation, a vibratory alarm, or any other type of electrical alarm, including an auditory alarm, a vibratory alarm or a pulsed alarm (dependent upon the pre-set frequency). Further, the alarm 16 may be an implantable, electrical stimulation device or the like. It should be understood that any suitable type of alarm may be utilized. With particular regard to the example of an auditory alarm, the auditory alarm may be positioned away from the user's ears, transmitting sound waves through the air, or may be fixed to the user such that sound waves are conducted through the user's skull. The particular audio signal transmitted may be in the form of a verbal message, such as "breathe deeply," for example, recorded in a pre-selected desired language. With regard to the pulsed alarm, the pulsing example utilizes a vibrator or other source of mechanical or electrical pulsing to generate vibrations through the skin, to the nerve endings, to generate a stimulating signal. Such a system may be utilized by patients with a hearing impairment or in situations where an audible alarm would be undesirable. In the case of electrical pulsed stimulation, the electrical voltage applied to the skin may be modulated by frequency, amplitude and duration. The processor 18 generates an alarm signal (step 114) for actuating the alarm 16 (actuation occurring at step 118) when measured BOS is less than or equal to the threshold BOS level, or, alternatively, with signal actuation being at regular intervals, based upon the calculated time period between low BOS occurrences, to raise the patient's level of consciousness. For the specific case of sleep apnea, rather than awakening the patient, the alarm 16 preferably only raises the level of consciousness of the patient in order to urge him or her to breathe, rather than bringing the patient to full consciousness and fully out of sleep.

In mammals and birds, sleep is divided into two broad types: Rapid Eye Movement (REM) and Non-Rapid Eye Movement (NREM or non-REM) sleep. Each type has a distinct set of associated physiological, neurological, and psychological features. The American Academy of Sleep Medicine (AASM) further divides NREM into three stages: N1, N2, and N3, the last of which is also called delta, or slow-wave, sleep (SWS). Sleep proceeds in cycles of REM and NREM, the order normally being from N1 to N2 to N3 to REM. There is a greater amount of deep sleep (stage N3) early in the night, while the proportion of REM sleep increases later in the night and just before natural awakening.

When the patient's blood oxygen saturation level is equal to or drops below the threshold level, rather than awakening the patient fully, the patient is stimulated by low-level vibration, pulsing, auditory sounds, electrical stimulation or the like so that he or she rises by one sleep level at a time until a sleep level is reached that allows alarm 16 to urge the patient's body to breathe and re-oxygenate the blood.

System 10 may record the occurrences of drop in blood oxygen saturation equal to or less than the threshold level, and calculate a period or cycle of BOS dips (step 112). This cycle may be a simple, arithmetic progression, or may be a complex, exponential moving average for a specified period of time. The alarm 16 is actuated based upon this cycle, which allows the system 10 to be used to train the patient to breathe to raise the blood oxygen above the threshold level. Once the period or cycle has been calculated, the system 10 may be used without the sensor 12, with the alarm 16 being actuated solely according to the calculated period.

In addition to calculation of the time period, and the subsequent generation of alarm signals, the alarm 16 may be actuated in direct response to the dip in BOS at or below the set threshold, thus actuating the alarm either according to the calculated period or in immediate response to a low measured BOS level. As a further alternative, rather than calculating a time and generating a signal at a regular period, the times of low-BOS occurrence may be recorded without calculation, with the stimulation signals being generated at set times rather than following the calculated time period (shown as dashed path 120 in FIG. 3). For example, if frequency of low-BOS occurrence is found to double with each hour for a particular patient, then the stimulation is provided following the cycle of low-BOS occurrence; i.e., the signal generation is doubled each hour, following the same cycle. Processor 18 may include learning or artificial intelligence programming, allowing for the calculation of irregular stimulation signal frequencies based upon the measurements provided by sensor 12 and recorded in memory 20.

The feedback of the periodic alarm generation is used to train the body to breathe according to the calculated time period throughout the patient's sleep, ultradian or circadian cycle. Additionally, rather than applying an alarm signal of equal intensity at all times, the alarm signal may have an intensity inversely proportional to (or following a desired function) the measured BOS. Thus, if the patient's measured BOS is not only less than or equal to the threshold level, but is trending towards a lower level, an alarm signal of relatively low intensity may be delivered to the patient with increasing signal intensity as BOS trends towards dangerously low levels. Thus, the patient receives an early warning signal and can take corrective breathing action.

As BOS rises, the alarm signal is not generated (following the comparison made in steps 106, 108), but if the BOS again lowers, as flow is returned again to steps 106 and 108, the alarm is actuated. As a data set is established, the time period actuates the alarm (i.e., in step 110, the time of occurrence is recorded, and alternative path 120 may be followed to actuate the alarm signal at step 114 based upon these set times). However, if low BOS occurs before the period of time is established, the low BOS will actuate the alarm, following the above process, and this low BOS will be recorded in the data set, also at step 110. A patient may have a regular fluctuation of BOS levels, and the calculated period of stimulation of the patient may also include a calculated intensity of stimulation for each stimulation time.

In addition to the oximeter or other sensor 12, additional physiological monitoring devices, such as a thermometer, sphygmomanometer, pulsemeter or the like, may be in communication with processor 18, since BOS is dependent upon a wide variety of factors, such as body temperature and blood pressure.

Additionally, diagnostic equipment or circuits may be integrated into system 10, or programmed as diagnostic routines within processor 18, in order to compensate for typical causes of abnormal readings in oximetry. For example, ambient light, jerky movements, incorrect positioning of the sensor, anemia, moisture, external heat, lower power or the like may all provide false or skewed measurements of BOS, thus activating a signal uniquely different from the low BOS signal, or may be compensated for by diagnostic routines or additional diagnostic and calibration equipment.

Additionally, a switch or button 28 may be provided for the user to temporarily deactivate the alarm 16. Switch or button 28 may be alternatively located on controller 14 or sensor 12. When the patient is in a near-sleep state, but not actually asleep, sleep apnea (or other breathing problems) may still occur. In order to train the patient's body to breathe properly, even when not asleep, the user is alerted to a low measured BOS level by the alarm 16, and then manually, temporarily deactivates the alarm by closing the switch or pressing the button 28. Alarm deactivation time periods may be customized by providing for multiple time input periods (at step 103), either for use with button 28 or as BOS rises after the alarm has been actuated. Thus, only the alarm stimulation required is applied to maintain satisfactory BOS.

It should be understood that the above system and method is not solely directed towards the treatment of sleep apnea, but towards any disorder or condition that causes the patient's blood oxygen saturation level to drop involuntarily, and which may be treated according to a regular cycle or by training the patient to breathe to maintain satisfactory BOS.

As noted above, for central sleep apnea and other medical conditions that periodically interrupt breathing impulses along the phrenic nerve, the system may include an implantable BOS sensing device in communication with an implantable controller that produces electrical impulses to implantable electrodes connected to the phrenic nerve or diaphramic nerve system. The BOS sensing device and controller may be separate units connected by wires or may be integrated into one unit. The BOS sensor is implanted in tissue with the required blood supply to obtain reliable BOS readings. The power source may also be implantable or external to the patient and charged or changed as required for the proper functioning of the nerve stimulation system.

Further, any medical condition that causes, or potentially causes, lowered blood oxygen requires continual monitoring, and when measured blood oxygen is equal to or below a specified value, the stimulation system 10 provides a patient the early awareness of lowering blood oxygen levels. Thus, as a result of awareness or conditioned reflex to the stimulation, improved breathing by the patient provides the air to the lungs required for maintaining blood oxygen at healthy levels. Therefore, the stimulation is particularly effective when used in conjunction with medication, breathing exercises, biofeedback, relaxation response and/or hypnosis.

It is to be understood that the present invention is not limited to the embodiments described above, but encompasses any and all embodiments within the scope of the following claims.

I claim:

1. A method of treating a breathing disorder, comprising the steps of:
    establishing a threshold blood oxygen saturation level;
    continually measuring blood oxygen saturation in a patient;
    continually comparing the measured blood oxygen saturation with the threshold blood oxygen saturation level;
    recording a time of low blood oxygen saturation occurrence in computer readable memory when the measured blood oxygen saturation is less than or equal to the threshold blood oxygen saturation level;
    calculating a time period between sequential times of low blood oxygen saturation occurrence;
    generating an alarm signal to actuate an alarm at regular intervals based upon the calculated time period to raise the patient's level of consciousness;
    generating the alarm signal when the measured blood oxygen saturation is less than or equal to the threshold blood oxygen saturation level; and
    establishing a period of time of deactivation of the alarm signal.

2. The method of treating a breathing disorder as recited in claim 1, further comprising the steps of:
    establishing a present time;
    comparing the present time with the time of deactivation; and generating a deactivation signal to override the alarm signal and deactivate an alarm.

3. The method of treating a breathing disorder as recited in claim 1, further comprising the step of recording the measured blood oxygen saturation when the measured blood oxygen saturation level is less than or equal to the threshold blood oxygen saturation level.

4. A breathing disorder treatment system, comprising:
a processor;
computer readable memory in communication with the processor, a threshold blood oxygen saturation level being recorded in the computer readable memory;
a blood oxygen saturation sensor for continually measuring a blood oxygen saturation level in a patient, the blood oxygen saturation sensor being in communication with the processor, the processor continually comparing signals from the sensor representing the measured blood oxygen saturation level with the threshold blood oxygen saturation level;
a clock circuit in communication with the processor for keeping time, the processor being programmed to record the time of low blood oxygen saturation occurrence in the computer readable memory when the measured blood oxygen saturation level is less than or equal to the threshold blood oxygen saturation level, the processor being programmed to calculate a time period between sequential times of low blood oxygen saturation occurrence;
an alarm in communication with the processor, the processor being programmed to generate an alarm signal actuating the alarm at regular intervals based upon the calculated time period in order to raise the patient's level of consciousness; and
means for selectively and temporarily deactivating said alarm.

5. The breathing disorder treatment system as recited in claim 4, wherein said alarm is an implantable electrical stimulator.

6. The breathing disorder treatment system as recited in claim 4, wherein said alarm is an vibratory alarm.

7. The breathing disorder treatment system as recited in claim 4, wherein said breathing disorder treatment system is adapted to be worn by the patient.

8. A method of treating a breathing disorder, comprising the steps of:
establishing a threshold blood oxygen saturation level;
continually measuring blood oxygen saturation in a patient;
continually comparing the measured blood oxygen saturation with the threshold blood oxygen saturation level;
recording a time of low blood oxygen saturation occurrence in computer readable memory when the measured blood oxygen saturation is less than or equal to the threshold blood oxygen saturation level;
calculating a frequency schedule of low blood oxygen saturation occurrence;
generating an alarm signal to actuate an alarm at multiple time intervals based upon the calculated frequency schedule of low blood oxygen saturation occurrence to raise the patient's level of consciousness;
generating the alarm signal when the measured blood oxygen saturation is less than or equal to the threshold blood oxygen saturation level; and
establishing a period of time of deactivation.

9. The method of treating a breathing disorder as recited in claim 8, further comprising the steps of:
establishing a present time;
comparing the present time with the time of deactivation; and
generating a deactivation signal to override the alarm signal to temporarily deactivate the alarm.

10. The method of treating a breathing disorder as recited in claim 8, further comprising the step of recording the measured blood oxygen saturation when the measured blood oxygen saturation level is less than or equal to the threshold blood oxygen saturation level.

11. A method of treating a breathing disorder, comprising the steps of:
establishing a threshold blood oxygen saturation level;
continually measuring blood oxygen saturation in a patient;
continually comparing the measured blood oxygen saturation with the threshold blood oxygen saturation level;
generating an alarm signal to actuate an alarm if the measured blood oxygen saturation is less than or equal to the threshold blood oxygen saturation level, the alarm having an intensity associated therewith, the intensity being proportional to the difference between the measured blood oxygen saturation and the threshold blood oxygen saturation level;
recording a time of low blood oxygen saturation occurrence in computer readable memory when the measured blood oxygen saturation is less than or equal to the threshold blood oxygen saturation level;
recording the measured blood oxygen saturation when the measured blood oxygen saturation level is less than or equal to the threshold blood oxygen saturation level; and
establishing a period of time of deactivation.

12. The method of treating a breathing disorder as recited in claim 11, further comprising the steps of:
establishing a present time;
comparing the present time with the time of deactivation; and
generating a deactivation signal to override the alarm signal to temporarily deactivate an alarm.

* * * * *